US006421563B1

(12) United States Patent
Sullivan et al.

(10) Patent No.: US 6,421,563 B1
(45) Date of Patent: Jul. 16, 2002

(54) SOLID-STATE MULTIPHASIC DEFIBRILLATION CIRCUIT

(75) Inventors: Joseph L. Sullivan, Kirkland; Lawrence A. Borschowa, Woodinville, both of WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

(21) Appl. No.: 09/516,426

(22) Filed: Mar. 1, 2000

(51) Int. Cl.[7] ................................................ A61N 1/39
(52) U.S. Cl. .......................................... 607/5; 428/908
(58) Field of Search .................... 607/4–5, 63, 142; 128/908

(56) References Cited

U.S. PATENT DOCUMENTS

| | | |
|---|---|---|
| 4,566,457 A | 1/1986 | Stemple |
| 4,827,936 A | 5/1989 | Pless et al. |
| 4,850,357 A | 7/1989 | Bach, Jr. |
| 5,033,467 A | 7/1991 | Bocchi et al. |
| 5,163,428 A | 11/1992 | Pless |
| 5,222,492 A | 6/1993 | Morgan et al. |
| 5,395,394 A | 3/1995 | Cameron |
| 5,470,341 A | 11/1995 | Kuehn et al. |
| 5,472,454 A | * 12/1995 | Ozawa ........................... 607/5 |
| 5,484,452 A | 1/1996 | Persson |
| 5,545,181 A | 8/1996 | Jacobson et al. |
| 5,594,287 A | 1/1997 | Cameron |
| 5,607,454 A | 3/1997 | Cameron et al. |
| 5,626,619 A | 5/1997 | Jacobson et al. |
| 5,749,904 A | 5/1998 | Gliner et al. |
| 5,769,872 A | 6/1998 | Lopin et al. |
| 5,772,689 A | 6/1998 | Kroll |
| 5,772,692 A | 6/1998 | Armstrong |
| 5,824,017 A | 10/1998 | Sullivan et al. |
| 6,230,054 B1 | * 5/2001 | Powers ........................... 607/5 |

FOREIGN PATENT DOCUMENTS

WO    WO98/47563    10/1998

OTHER PUBLICATIONS

PCT International Search Report, dated Sep. 11, 2001, for PCT/US 01/05686.

* cited by examiner

*Primary Examiner*—Kennedy Schaetzle
*Assistant Examiner*—Kristen Droesch
(74) *Attorney, Agent, or Firm*—Christensen O'Connor Johnson Kindness PLLC

(57) ABSTRACT

A solid-state defibrillation circuit for applying a multiphasic defibrillation pulse to a patient is disclosed. The circuit eliminates the need for a mechanical relay, and provides for a current limiting circuit for limiting leakage currents that would otherwise flow to the patient from the solid-state components, and for preventing the short-circuiting of a defibrillation pulse from a second defibrillator. In one embodiment, the output circuit of the defibrillator comprises an H-bridge, and the current limiting circuit comprises a plurality of resistors coupled in parallel with each of the legs of the H-bridge. The plurality of resistors allow current flow which reduces the voltage potential across the patient that is caused by the leakage currents through the output circuit. The current limiting circuit also includes a shunt resistor for shunting leakage currents away from the patient. The current limiting circuit also includes a non-linear element, such as an MOV or tranzorb in series with the output of the defibrillation circuit for limiting the leakage currents. The current limiting circuit also includes a diode coupled in series with one of the solid-state switches of the output circuit, for helping prevent voltage breakdown across the switches of the output circuit when an external energy shock is applied from an outside source, such as from a second defibrillator.

15 Claims, 6 Drawing Sheets

SOLID-STATE MULTIPHASIC DEFIBRILLATION CIRCUIT

FIELD OF THE INVENTION

This invention relates generally to apparatus for generating defibrillation waveforms, and more particularly to a solid-state circuit for generating a multiphasic defibrillation waveform in an external defibrillator.

BACKGROUND OF THE INVENTION

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a mechanical high-energy transfer relay. A discharge control signal causes the mechanical relay to complete an electrical circuit between the storage capacitor and a wave shaping circuit whose output is connected to the electrodes attached to the patient.

The American Heart Association has recommended a range of energy levels for the first three defibrillation pulses applied by an external defibrillator. The recommended energy levels are: 200 joules for a first defibrillation pulse; 200 or 300 joules for a second defibrillation pulse; and 360 joules for a third defibrillation pulse, all within a recommended variance range of no more than plus or minus 15 percent according to standards promulgated by the Association for the Advancement of Medical Instrumentation (AAMI). These high-energy defibrillation pulses are required to ensure that a sufficient amount of the defibrillation pulse energy reaches the heart of the patient, after accounting for energy dissipated in the chest wall of the patient.

The mechanical relay used in contemporary external defibrillators has traditionally allowed a monophasic waveform to be applied to the patient. It has recently been discovered, however, that there may be certain advantages to applying a biphasic, rather than a monophasic, waveform to the patient. For example, preliminary research indicates that a biphasic waveform may limit the resulting heart trauma associated with the defibrillation pulse.

One prior art circuit for generating a biphasic waveform of the energy levels recommended by the American Heart Association is illustrated in U.S. Pat. No. 5,824,017, which is hereby incorporated by reference. FIG. 1 of U.S. Pat. No. 5,824,017 has been reproduced as FIG. 1 herein. The circuit of FIG. 1 shows a defibrillator 8 which includes a mechanical relay 35. As will be described in more detail below, in order to make the defibrillator 8 into an entirely solid-state defibrillator, the mechanical relay 35 would have to be replaced with a solid-state relay or else eliminated. However, certain problems such as leakage currents would be associated with an entirely solid-state defibrillator. In order to provide a better understanding of the problems associated with an entirely solid-state defibrillator, the structure and operation of the circuit of FIG. 1 will now be described in detail.

FIG. 1 includes a block diagram of an external defibrillator 8 that is connected to a patient 16. The defibrillator includes a microprocessor 20 that is connected to an energy storage capacitor 24 via a charging circuit 18. During the operation of the defibrillator 8, the microprocessor 20 controls the charging circuit 18 by a signal on a control line 25 to charge the energy storage capacitor 24 to a desired voltage level. In order to generate the necessary defibrillation pulse for external application to a patient, the energy storage capacitor 24 is charged to between 100 volts and 2,200 volts. To monitor the charging process, the microprocessor 20 is connected to a scaling circuit 22 by a pair of measurement lines 47 and 48, and by a control line 49. The scaling circuit 22 is connected to the energy storage capacitor 24 by a bridge line 28, which connects to the negative lead of the capacitor 24, and by a line 30, which connects to the positive lead of the capacitor 24. A clock 21 is also connected to the microprocessor 20.

After charging to a desired level, the energy stored in the energy storage capacitor 24 may be delivered to the patient 16 in the form of a defibrillation pulse. An output circuit 14 is provided to allow e controlled transfer of energy from the energy storage capacitor 24 to the patient 16. The output circuit 14 includes four switches 31, 32, 33, and 34, each switch on a leg of the output circuit 14 arrayed in the form of an "H" (hereinafter the "H-bridge" output circuit). Switches 31 and 33 are coupled through a protective component 27 to the positive lead of the energy storage capacitor 24 by a bridge line 26. The protective component 27 has both inductive and resistive properties, and thereby limits the current and voltage changes from the energy storage capacitor 24.

Switches 32 and 34 are coupled to the energy storage capacitor 24 by a bridge line 28. The patient 16 is connected to the left side of the H-bridge by an apex line 17, and to the right side of the H-bridge by a sternum line 19. As depicted in FIG. 1, the apex line 17 and the sternum line 19 are connected to electrodes 15A and 15B, respectively, by a patient isolation relay 35. The microprocessor 20 is connected to the switches 31, 32, 33, and 34 by control lines 42A, 42B, 42C, and 42D, respectively, and to the patient isolation relay 35 by control line 36. Application of appropriate control signals by the microprocessor 20 over the control lines causes the switches of the output circuit 14 to be appropriately opened and closed (described in more detail below), whereby the output circuit 14 conducts energy from the energy storage capacitor 24 to the patient 16.

In order to conduct a first phase of a biphasic pulse from the energy storage capacitor 24 to the patient 16, switches 31 and 32 are closed along with relay 35. Thus, during the first phase, energy travels from the positive terminal of the capacitor 24 down through switch 31, out lines 17 and 15A to the patient 16, and then back from the patient 16 through lines 15B and 19, down through switch 32 to the negative terminal of the capacitor 24. The first phase is ended by opening switches 31 and 32 before the capacitor 24 is completely discharged. Then the second phase of the biphasic defibrillation pulse is begun by closing switches 33 and 34 with relay 35 also closed. Thus, during the second phase, energy travels from the positive terminal of the storage capacitor 24 down through switch 33, out lines 19 and 15B to the patient 16, and then back from the patient 16 through lines 15A and 17, and down through switch 34 to the negative terminal of the capacitor 24. It can be seen with reference to FIG. 1 that the travel of energy through the patient 16 during the first phase of the biphasic defibrillation pulse is opposite in direction to the travel of energy through the patient 16 during the second phase of the biphasic defibrillation pulse.

The mechanical relay 35 is a large, expensive, and relatively finicky component. It would be desirable to eliminate the mechanical relay if possible and replace it with solid-state switches, or else eliminate it altogether. However, there are at least two problems with either of these solutions. The first problem has to do with leakage currents, and the second problem has to do with the shorting of a defibrillation pulse from a simultaneously connected second defibrillator.

Leakage currents are relatively small currents that flow through solid-state devices even when they are supposed to be in the off state. For example, solid-state devices such as SCRs and IGBTs in some applications may have a leakage current of around 1 milliamp. In a mechanical relay, no leakage currents occur because the mechanical contacts and blades of the mechanical relay are physically separated from one another when the relay is open, thus preventing any current from flowing. In contrast, in solid-state devices, leakage currents can occur because solid-state devices by definition have no moving parts that can be physically separated. Instead, solid-state devices typically rely on gate voltages or similar phenomena to control the current flow. Even with the gate voltages all the way off, a small amount of leakage current usually still results through the semiconductor elements.

With reference to FIG. 1, if the relay 35 was made to be solid-state, one path in the output circuit 14 through which the leakage currents would reach the patient 16 is from the positive terminal of the capacitor 24, through solid-state switch 31, down through line 17, through a solid-state switch at relay 35, through line 15A, through the patient 16 and back through line 15B, through another solid-state switch at relay 35 to line 19, down through switch 32 and back via line 28 to the negative terminal of the capacitor 24. With leakage currents of about 1 milliamp, this creates a leakage current through the patient of about 1 milliamp, which is far greater than the acceptable 100 microamp current in an external defibrillator for the patient. The acceptable leakage current in other circumstances may be even less (e.g., the acceptable leakage current for direct defibrillation during surgery may be 10 microamps or less).

Another problem with substituting solid-state switches for the mechanical relay is the short circuiting of a defibrillation pulse from a simultaneously attached second defibrillator. In other words, the situation may sometimes occur where once a first defibrillator is connected to a patient in an emergency situation by a first emergency response team, a second defibrillator may be connected to the patient at a later time by a second emergency response team while the first defibrillator is still attached. In such a circumstance, the switches of the first defibrillator circuitry must be able to withstand a shock from the second defibrillator, without breaking down and allowing the defibrillation shock from the second defibrillator to short circuit through the first defibrillator circuitry rather than being applied to the patient.

More specifically, as shown in FIG. 1, if a second defibrillator were hooked across the patient 16 such that its electrodes were coupled to the same general areas of the patient as the electrodes 15A and 15B, a defibrillation pulse from the second defibrillator could short circuit through the relay 35 to line 17, down switch 34, up switch 32 to line 19 such that the energy would travel through this path rather than through the patient 16. Alternatively, the energy could short circuit through the relay 35 through line 17 up through switch 31, down through switch 33 and out through line 19 and out through relay 35, rather than traveling through the patient 16. This is only a problem when solid-state switches are used that often do not have high enough voltage tolerances to withstand a shock from another external defibrillator. This was not generally a concern with mechanical relays because the physical separation of the relay components helped prevent voltage breakdown across the relay.

The present invention is directed to providing an apparatus that overcomes the foregoing and other disadvantages. More specifically, the present invention is directed to a solid-state defibrillation circuit that limits undesired currents through the defibrillator.

SUMMARY OF THE INVENTION

A solid-state defibrillation circuit that allows a multiphasic defibrillation pulse to be discharged to a patient from an energy storage device, preferably an energy storage capacitor, is disclosed. The defibrillation circuit applies the defibrillation pulse to the patient through an output circuit and electrodes when the electrodes are coupled to the patient. The defibrillation circuit also includes a current limiting circuit that limits the leakage currents that flow to the patient and that also prevents short circuiting of currents from a second defibrillator.

In accordance with one aspect of the invention, the current limiting circuit comprises a plurality of resistors coupled to the solid-state output circuit. In an embodiment where the output circuit is in the form of an H-bridge, the current limiting circuit includes a resistor coupled in parallel with each leg of the H-bridge. Leakage currents from the solid-state relay switches will be distributed through the resistors, causing the leakage currents flowing through the output circuit to become more balanced across the H-bridge. This current distribution reduces the voltage differential between the circuit nodes to which the electrodes are coupled. In this manner, leakage currents to the patient are reduced. The leakage currents are preferably reduced to a level of 100 microamps or less.

In accordance with another aspect of the invention, the current limiting circuit includes a shunt resistor coupled between the circuit nodes that are coupled to the electrodes. The shunt resistor is designed to shunt leakage currents away from the patient. In one embodiment, the shunt resistor has a value of about 1 Kohm.

In accordance with another aspect of the invention, the current limiting circuit includes a non-linear element, such as an MOV or a tranzorb, in series with the defibrillator output. These elements limit leakage currents by conducting very little current below a threshold voltage. Normal defibrillator operation is allowed in that the elements conduct normal current when high voltages are present.

In accordance with yet another aspect of the invention, the current limiting circuit includes a diode coupled in series with one of the switches of the output circuit. The function of the diode is to prevent voltage breakdown when a high-energy shock is applied from an external source, such as from a second defibrillator.

It will be appreciated that the disclosed solid-state multiphasic defibrillation circuit is advantageous in that it eliminates the need for a mechanical relay that can be large, expensive, and difficult to control.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
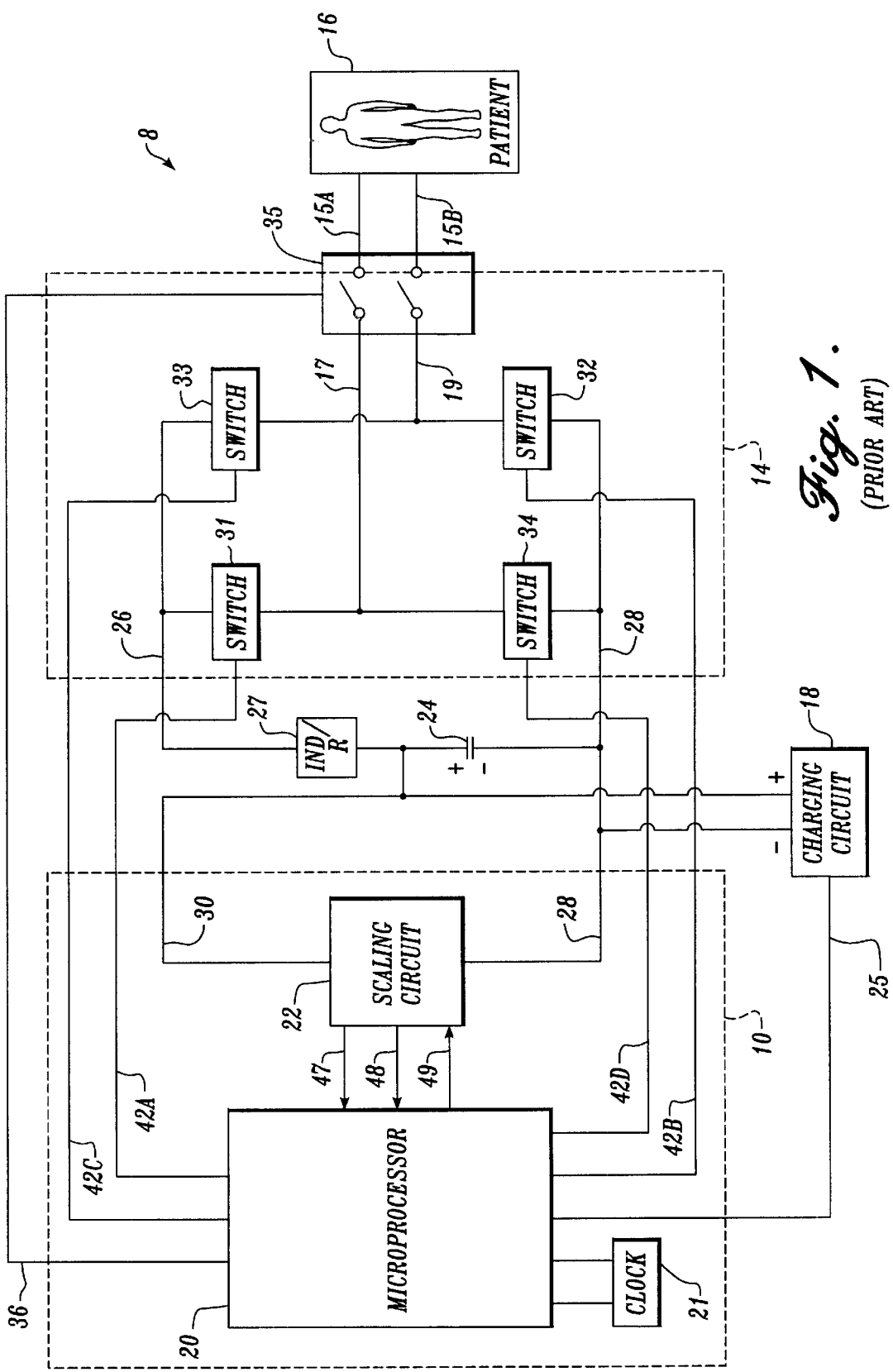
FIG. 1 is a block diagram of a prior art multiphasic external defibrillator.
Figure 2:
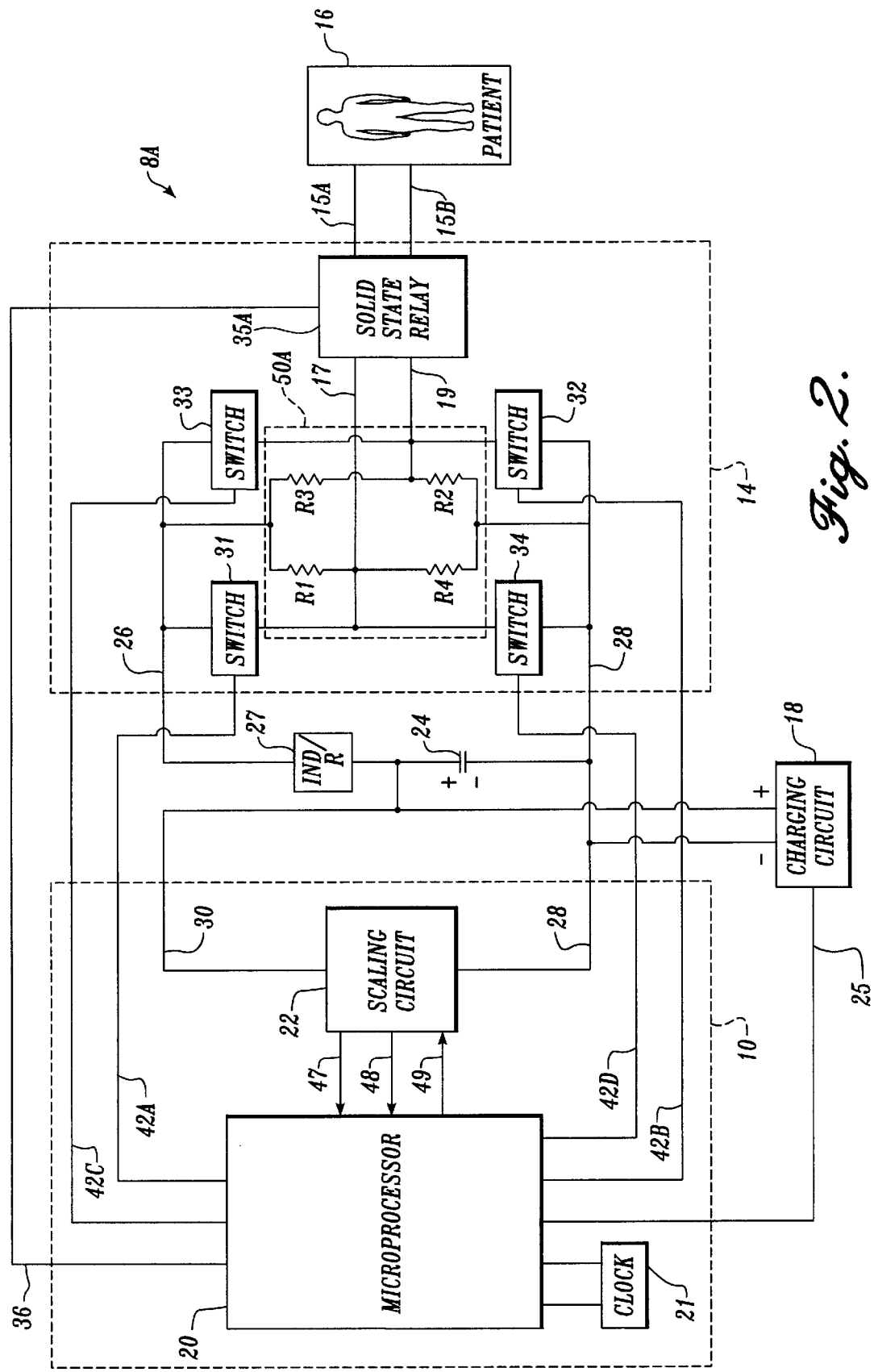
FIG. 2 is a schematic diagram of a solid-state multiphasic external defibrillator having an output circuit formed in accordance with the present invention, including balancing resistors.

FIG. 2 is a schematic diagram of an external defibrillator 8A that includes a solid-state relay 35A and a current limiting circuit 50A. The solid-state relay 35A may include one or more solid-state switches, and acts to complete the circuit path between the output circuit 14 and the patient 16. As will be described below with reference to FIG. 6, in an alternate embodiment the solid-state relay 35A may be eliminated entirely. The remaining components of the defibrillator 8A of FIG. 2 are similar to those of the defibrillator 8 of FIG. 1.

As illustrated in FIG. 2, the current limiting circuit 50A includes four resistors, R1 to R4. These resistors are designed to address the problem of leakage currents. Resistors R1 to R4 are referred to as balancing resistors. Resistor R1 is coupled in parallel with switch 31, resistor R2 is coupled in parallel with switch 32, resistor R3 is coupled in parallel with switch 33, and resistor R4 is coupled in parallel with switch 34. As will be described in more detail below, these resistors help reduce the voltage differential between the sternum line 17 and the apex line 19, so as to reduce the leakage currents to the patient 16. The function of the resistors R1 to R4 will be discussed primarily through a series of mathematical examples.

The initial example is described with respect to the solid-state switches 31 to 34 having leakage currents associated with them. If the leakage currents and the voltage drops across each switch are identical, then according to common circuit analysis, these leakage currents will not produce a voltage differential between the apex line 17 and the sternum line 19. If however, different leakage currents and voltage drops are found for different ones of the switches 31 to 34, then a voltage differential will result between the apex line 17 and the sternum line 19. Such a voltage differential can produce leakage currents through the patient 16.

One method for analyzing how the resistors R1 to R4 alleviate the voltage differential problem is to simulate the switches 31 to 34 as resistors, and apply common circuit node analysis. The resistor values represent the effective impedance of the switches when they are in the "off" state. In the following equations, the symbols are designated as follows:

$R_{31}$=the simulated resistance across switch 31.

$R_{32}$=the simulated resistance across switch 32.

$R_{33}$=the simulated resistance across switch 33.

$R_{34}$=the simulated resistance across switch 34.

$V_{17}$=the voltage at the H-bridge node coupled to apex line 17.

$V_{19}$=the voltage at the H-bridge node coupled to sternum line 19.

$V_{cap}$=the capacitor voltage on line 26 (the voltage on line 28 is referenced as zero).

$R_P$=the simulated resistance across the solid-state relay 35A and the patient 16 (i.e., between apex line 17 and sternum line 19).

With these definitions, the circuit node analysis equation for the $V_{17}$ node is:

$$\frac{(V_{CAP} - V_{17})}{R_{31}} - \frac{(V_{17} - V_{19})}{R_P} - \frac{(V_{17} - 0)}{R_{34}} = 0 \qquad (1)$$

Then by multiplying by $R_{31}R_{34}R_P$ and combining terms:

$$V_{cap}(R_{34}R_P) - V_{17}(R_{31}R_P + R_{31}R_{34} + R_{34}R_P) + V_{19}(R_{31}R_{34}) = 0 \qquad (2)$$

Further, the circuit node analysis equation for the $V_{19}$ node is:

$$\frac{(V_{CAP} - V_{19})}{R_{33}} + \frac{(V_{17} - V_{19})}{R_P} - \frac{(V_{19} - 0)}{R_{32}} = 0 \qquad (3)$$

And by multiplying by $R_{32}R_{33}R_P$ and combining terms:

$$V_{CAP}(R_{33}) + V_{17}(R_{32}R_{33}) - V_{19}(R_{32}R_P + R_{32}R_{33} + R_{33}R_P) = 0 \qquad (4)$$

Since the purpose of these examples is to illustrate the effect of changing the resistor values, the following simple values are used in this first case to solve for $V_{17}$ and $V_{19}$:

$$V_{cap}=1V; R_P, R_{31} \text{ and } R_{32}=1 \text{ ohm}; R_{33} \text{ and } R_{34}=2 \text{ ohms} \qquad (5)$$

Substituting these values into equation (2) yields:

$$2-5V_{17}+2V_{19}=0 \qquad (6)$$

And substituting into equation (4) yields:

$$1+2V_{17}-5V_{19}=0 \qquad (7)$$

Further, solving for (6) and (7) yields:

$$V_{17}=4/7 \text{ and } V_{19}=3/7, \text{ thus } V_{17}-V_{19}=1/7 \qquad (8)$$

This example th us shows a voltage differential between apex line 17 and sternum line 19 of 1/7 volts, which equals 0.14286 volts.

Now, to see the effect of using the balanced bridge resistors R1 to R4 of FIG. 2, assume R1 to R4 all equal 1 ohm. The above equations may be kept essentially the same, except that the values for the resistances should now be calculated with an additional 1 ohm resistor in parallel. Thus, $R_{31}$ and $R_{32}$ at 1 ohm in parallel with another 1 ohm will be calculated as:

$$\frac{1 \times 1}{1+1} = \frac{1}{2} \qquad (9)$$

Similarly, $R_{33}$ and $R_{34}$ at 2 ohms in parallel with 1 ohm will be calculated as:

$$\frac{1 \times 2}{1+2} = \frac{2}{3} \qquad (10)$$

Substituting these values into equation (2) yields:

$$4-9V_{17}+2V_{19}=0 \qquad (11)$$

and substituting into equation (4) yields:

$$3+2V_{17}-9V_{19}=0 \qquad (12)$$

Further, solving for equations (11) and (12) yields:

$$V_{17}=6/11 \text{ and } V_{19}=5/11, \text{ thus } V_{17}-V_{19}=1/11 \qquad (13)$$

Thus, when the balancing resistors R1 to R4 are used, this example shows a voltage differential between apex line 17 and sternum line 19 of 1/11 volts, which equals 0.09091 volts. Thus, the addition of the balancing resistors R1 to R4 was able to reduce the voltage differential between the apex line 17 and the sternum line 19 from 0.14286 volts to 0.09091 volts. As stated above, these values are given for purposes of illustration only. The demonstrated reduction in voltage differential illustrates th e reduced potential for leakage currents to the patient 16. In one embodiment, resistors R1–R4 have a value of 1 megohm, although values ranging from 10 Kohms to 10 megohms may be suitable. Lower values tend to reduce the voltage differential between the apex line 17 and the sternum line 19.

It is understood that the values for the balancing resistors R1 to R4 can be selected so as to optimize the balancing process, while attempting to minimize the minor current drain that occurs from the capacitor 24 through the resistive paths. In an embodiment where one or more of the switches 31 to 34 are of different types, one or more of the resistors R1 to R4 may be given different values so as to best balance the predicted leakage currents from the switches.

Figure 3:
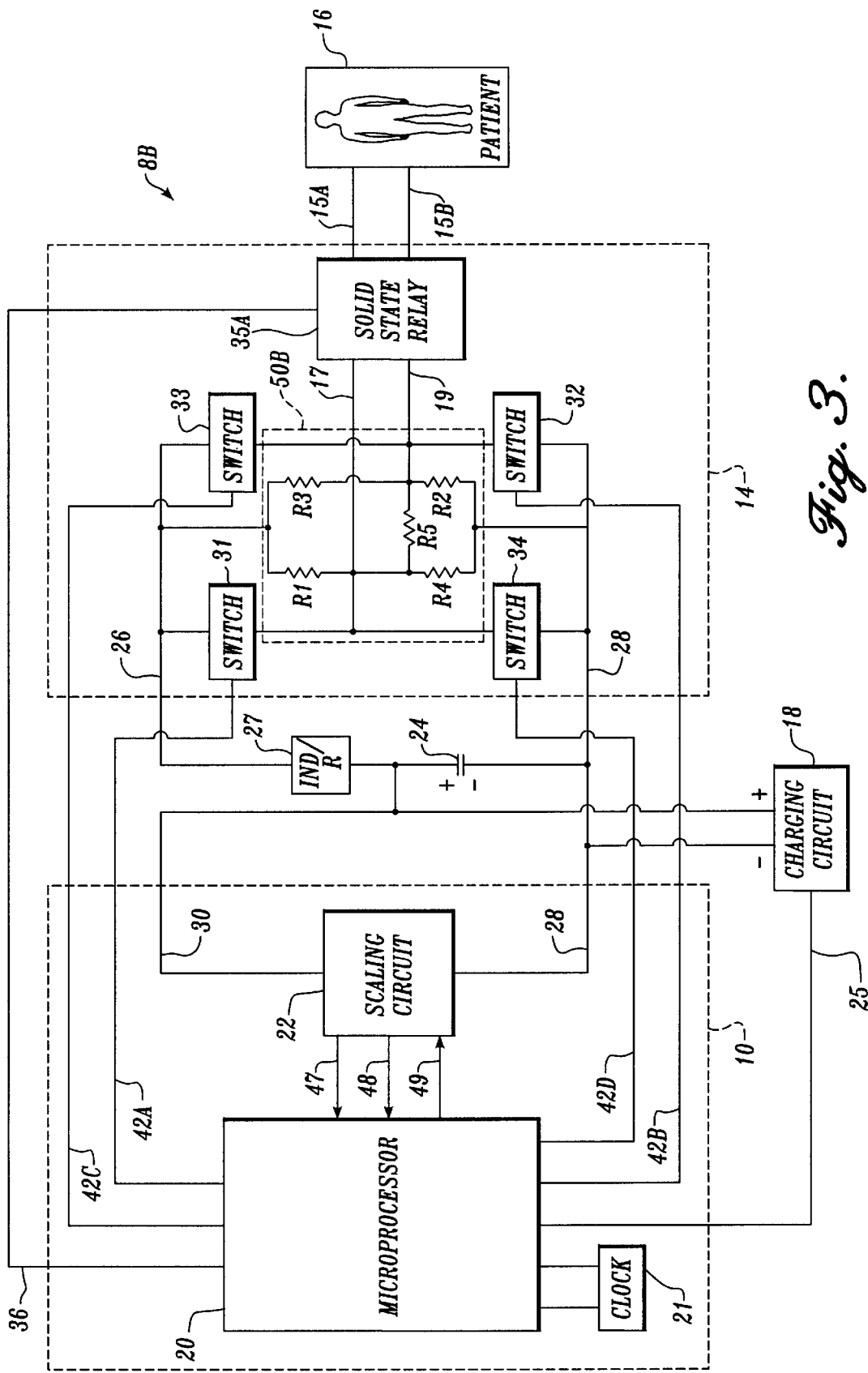
FIG. 3 is a schematic diagram of a solid-state multiphasic external defibrillator having an output circuit formed in accordance with the present invention, including a shunt resistor.

As illustrated in FIG. 3, in a defibrillator 8B a current limiting circuit 50B also includes a shunt resistor R5. Shunt resistor R5 is coupled between the apex line 17 and the sternum line 19. Shunt resistor R5 is designed to shunt leakage currents away from the patient 16. Shunt resistor R5 generally has a value of about 1 Kohm because during the off state, the effective impedance of the patient with respect to the leakage current may be several thousand ohms, while during the defibrillation procedure, the effective patient impedance is usually less than 100 ohms. Thus, a 1 Kohm shunt resistor will shunt most of the current during the off state, and allow the patient to receive most of the current during a defibrillation pulse.

Figure 4:
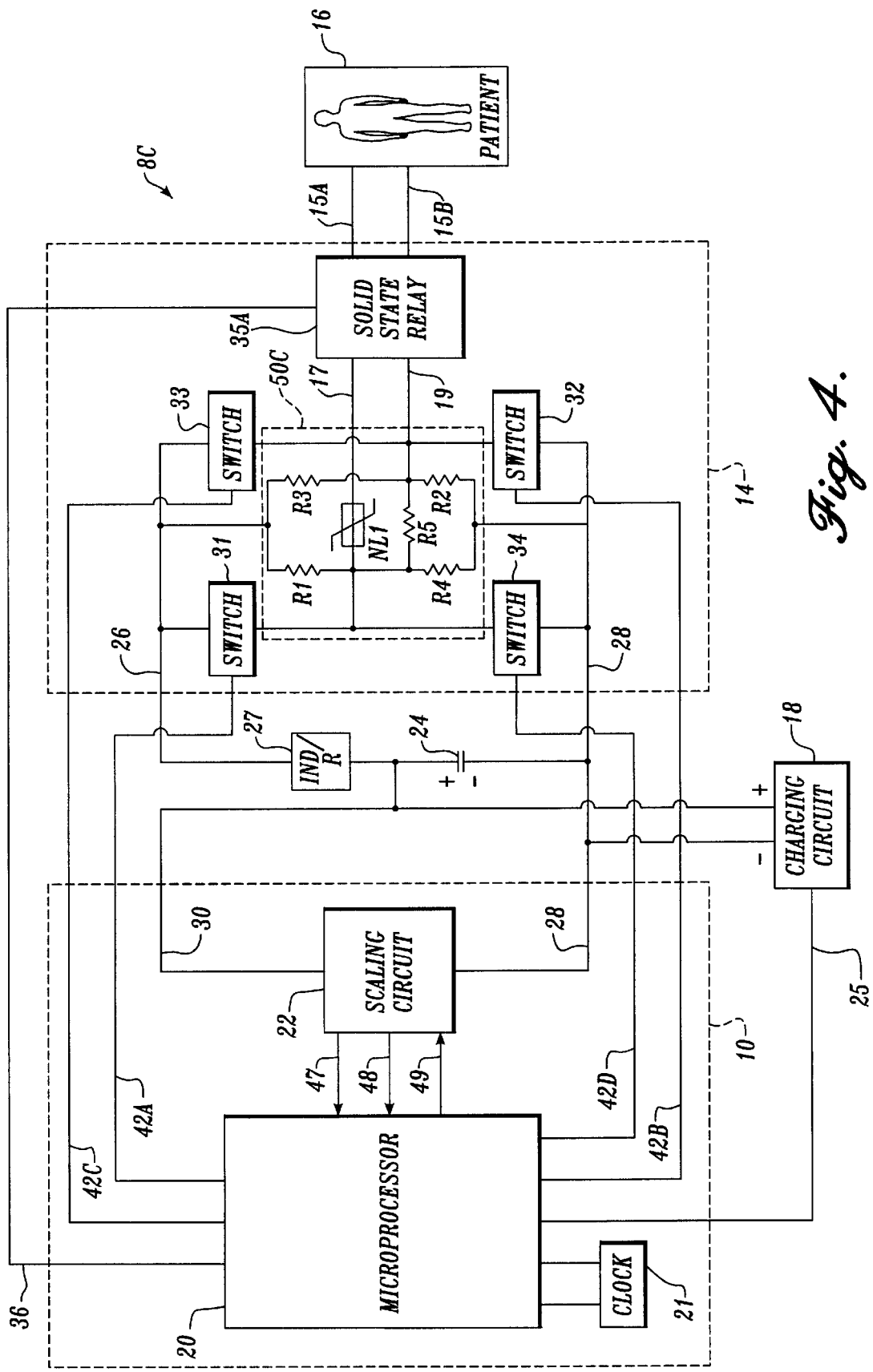
FIG. 4 is a schematic diagram of a solid-state multiphasic external defibrillator having an output circuit formed in accordance with the present invention, including a nonlinear element.

As illustrated in FIG. 4, in a defibrillator 8C a current limiting circuit 50C also includes a nonlinear element NL1, such as an MOV or a tranzorb, in series with the output. These elements conduct very little current below a threshold voltage, but conduct high currents above the threshold. Thus, when a defibrillation pulse is being applied to the patient, the nonlinear elements would allow proper defibrillation operation; however, when only low voltages were present during the off state, the leakage currents would be limited.

Figure 5:
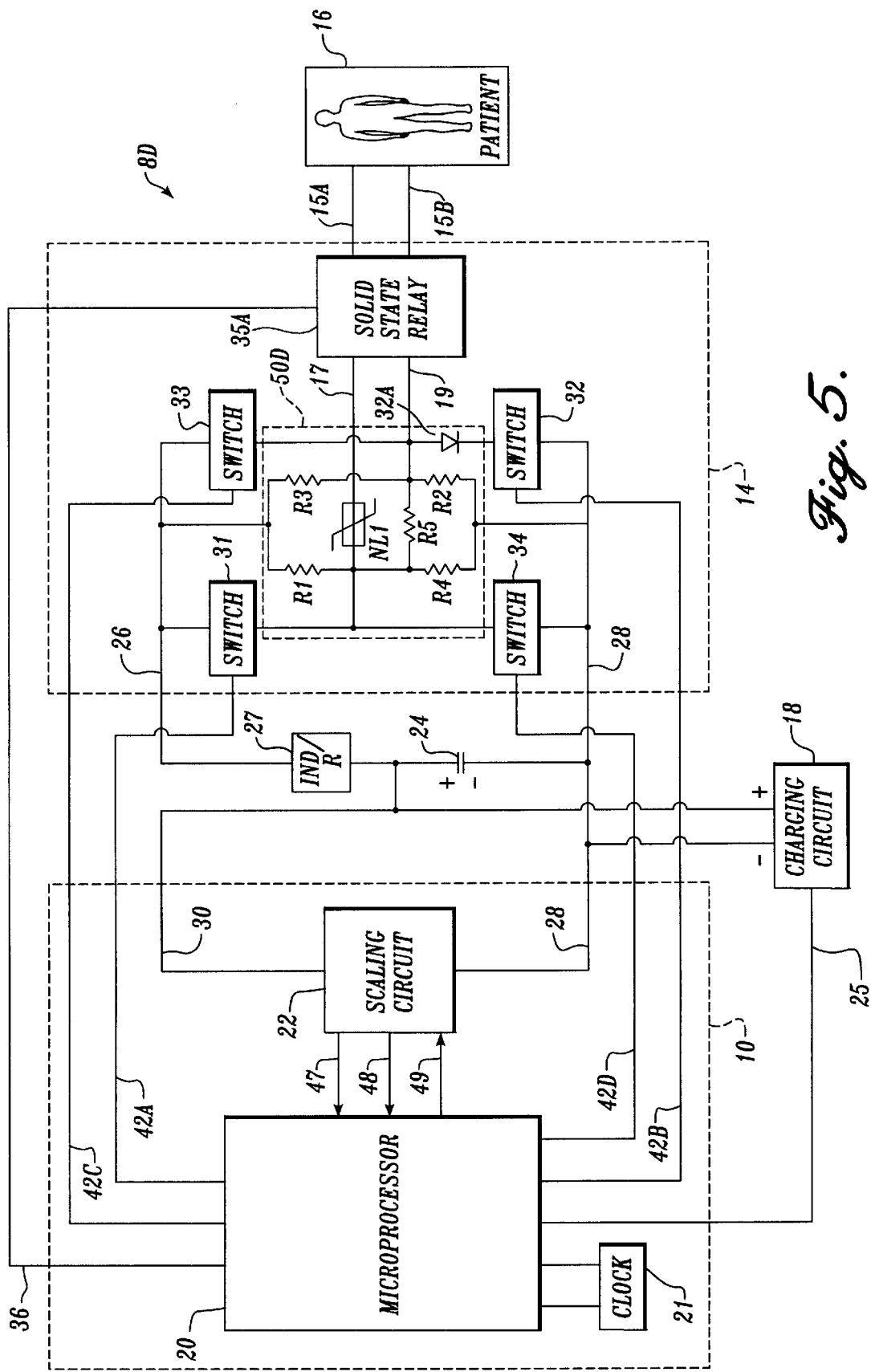
FIG. 5 is a schematic diagram of a solid-state multiphasic external defibrillator having an output circuit formed in accordance with the present invention, including a diode.

As illustrated in FIG. 5, in a defibrillator 8D a current limiting circuit 50D also includes a diode 32A, designed to address the problem of the short circuiting of a second defibrillator. The function of the diode 32A can be described with respect to the types of switches used for switches 31, 32, 33, and 34. In one embodiment, switches 31, 33, and 34 are SCR type switches. As required for the biphasic operation, the fourth switch 32 is a type that can shut off energy flow, such as a pair of IGBT switches. In this configuration the diode 32A helps stand off the voltage from a second defibrillator. For example, the voltage from a third-party defibrillator may be approximately 4,000 volts. The SCR switches can stand off 2,300 volts in each direction. However, the IGBTs can only stand off 2,400 volts in the forward direction. Therefore, if a pulse is applied by a second defibrillator of 4,000 volts in the reverse direction, the IGBTs breakdown, thus leaving the single SCR switch to stand off 4,000 volts, which it is incapable of doing. When the SCR breaks down, a short circuit is caused such that the defibrillation pulse from the second defibrillator short circuits through the circuitry of the first defibrillator as described above rather than being applied to the patient. However, with the diode 32A inserted in the circuit as illustrated in FIG. 2, it allows the IGBTs 32 to stand off the voltage in the reverse direction, such that no short circuiting occurs. In one embodiment, the diode 32A is a part number K40S from Voltage Multipliers Inc. of Visalia, Calif., which has a 4000 volt reverse breakdown voltage and a 150 amp surge capability. In an alternate embodiment to FIG. 2, an all IGBT H-bridge could be used, if each IGBT leg also included a series diode such as diode 32A.

Figure 6:
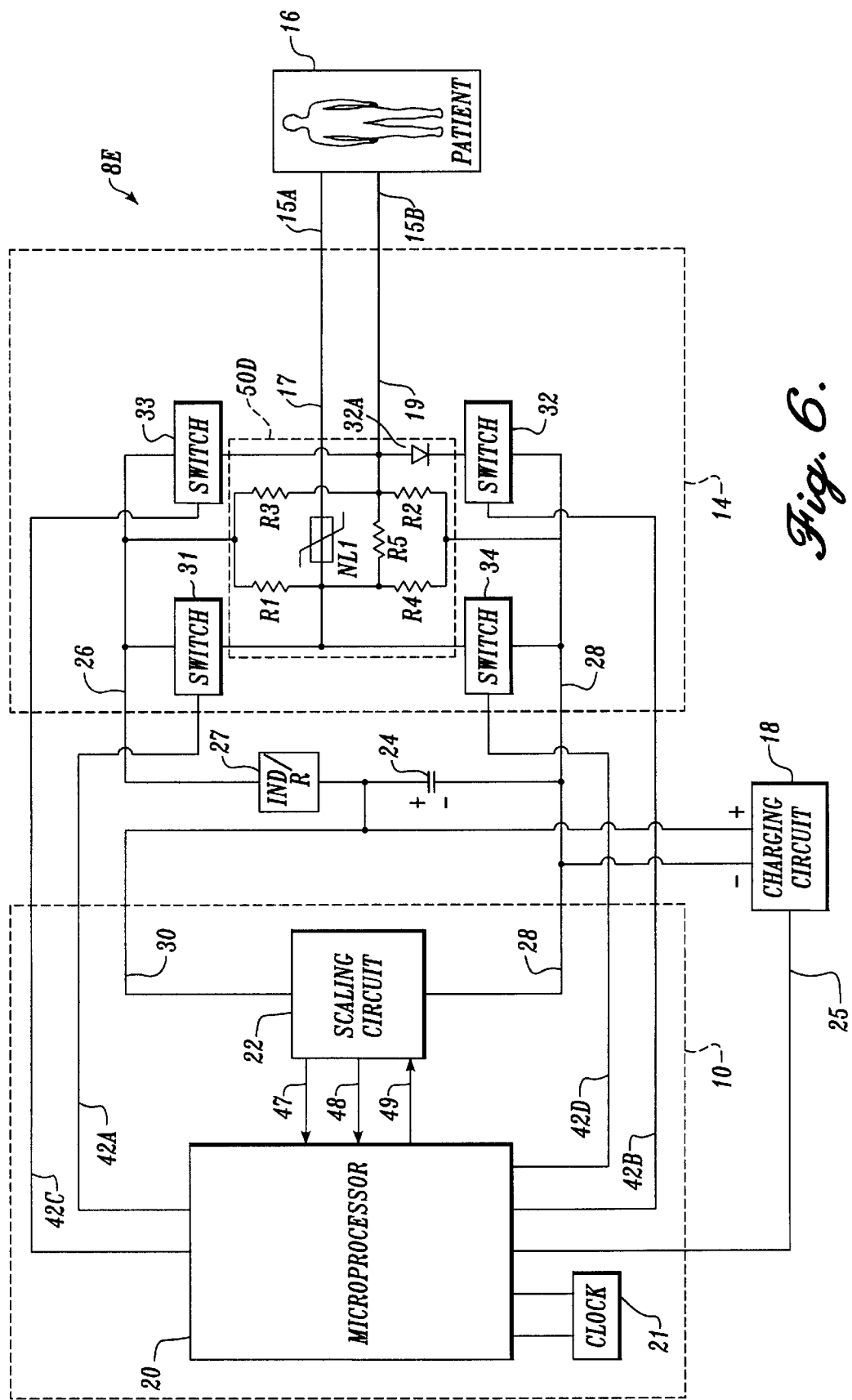
FIG. 6 is a schematic diagram of a solid-state multiphasic external defibrillator having an output circuit formed in accordance with the present invention, in which the solid-state relay has been eliminated.

As illustrated in FIG. 6, in a defibrillator 8E it is shown that the solid-state relay 35A may in some cases be eliminated entirely. By using a solid-state output circuit, the switches 31–34 of the output circuit may be used to control the delivery of the defibrillation currents to the patient 16, without requiring the use of a relay. The various current limiting elements of the output circuit 50D, including the resistors R1–R5, the nonlinear element NL1, and the diode 32A, help reduce the possibilities of leakage currents and the short circuiting of a second defibrillator, such that the relay 35 may in some cases be eliminated.

While the preferred embodiment of the invention has been illustrated and described, it will be appreciated that various changes can be made therein without departing from the spirit and scope of the invention. The present invention has been described in relation to a preferred embodiment and several variations. One of ordinary skill after reading the foregoing specification will be able to effect various changes, alterations, and substitutions of equivalents without departing from the broad concepts disclosed. It is therefore intended that the scope of the letters patent granted hereon be limited only by the definition contained in the appended claims and equivalents thereof, and not by limitations of the embodiments described thereof.

The embodiments of the invention in which an exclusive property or privilege is claimed are defined as follows:

1. A circuit for limiting leakage currents in a defibrillator having first and second circuit nodes for being coupled to a patient, comprising:
   (a) a first branch coupled to the first circuit node configured to conduct current from the first circuit node when the defibrillator is not generating a multiphasic defibrillation pulse; and
   (b) a second branch coupled to the second circuit node configured to conduct current from the second circuit node when the defibrillator is not generating a multiphasic defibrillation pulse, the first and second branches conducting current from the first and second nodes so as to reduce the voltage potential across the first and second nodes and thereby reduce leakage currents conducted to the patient;

wherein the first and second branches each comprise two resistors in series, the branches being coupled to the circuit nodes at the node between the two resistors.

2. The circuit of claim 1, wherein the circuit further comprises a resistor coupled between the first and second circuit nodes of the defibrillator.

3. The circuit of claim 1, wherein the two resistors in series in each of the two branches are of approximately the same resistive values.

4. The circuit of claim 1, wherein the first and second branches are coupled in parallel with one another.

5. In an external defibrillator for applying a multiphasic defibrillation pulse to a patient through first and second electrodes when the first and second electrodes are coupled to a patient, the external defibrillator having an energy storage device for storing the energy to be conducted to the patient in the form of a defibrillation pulse, the external defibrillator also including a multiphasic output circuit having a plurality of solid-state switches for coupling the energy storage device to the electrodes, the improvement comprising:

a current limiting circuit coupled to the multiphasic output circuit for limiting the flow of leakage currents through selected portions of the multiphasic output circuit when the defibrillator is not applying a defibrillation pulse to the patient;

wherein the current limiting circuit comprises a plurality of resistors coupled to the multiphasic output circuit for conducting at least a portion of the leakage currents from the multiphasic output circuit so as to reduce the voltage potential across the first and second electrodes, and wherein the multiphasic output circuit is in an H-bridge configuration, and the plurality of resistors of the current limiting circuit comprise at least one resistor coupled in parallel with each of the legs of the H-bridge.

6. The improvement of claim 5, wherein the current limiting circuit further comprises a resistor coupled between the first and second electrodes.

7. The improvement of claim 5, wherein the current limiting circuit further comprises a non-linear element coupled in the circuit path between the output circuit and the electrodes for conducting minimal current below a threshold voltage, but normal current above the threshold voltage.

8. The improvement of claim 5, wherein one of the plurality of switches of the multiphasic output circuit comprises a transistor, the current limiting circuit further comprising a diode coupled in series with the insulated gate bipolar transistor for preventing voltage breakdown in the event that an external energy shock is applied to the defibrillator from an outside source, such as from a second defibrillator.

9. The method of claim 5, wherein the current limiting circuit limits the leakage currents that flow to the patient to approximately 100 microamps or less.

10. A solid-state multiphasic defibrillator, comprising:

(a) first and second electrodes configured to conduct the energy of a multiphasic defibrillation pulse to a patient when the first and second electrodes are coupled to the patient;

(b) a solid-state multiphasic output circuit having first and second circuit nodes, the first circuit node being coupled to the first electrode and the second circuit node being coupled to the second electrode; and (c) a current limiting circuit including first and second branches, the first branch being coupled to the first circuit node of the solid-state multiphasic output circuit, and the second branch being coupled to the second circuit node of the solid-state multiphasic output circuit;

wherein the first and second branches of the current limiting circuit each provide a path for current flow when the defibrillator is not applying a defibrillation pulse to the patient so as to reduce the voltage differential across the first and second circuit nodes of the output circuit when the defibrillator is not applying a multiphasic defibrillation pulse, and wherein the first and second branches of the current limiting circuit comprise a plurality of resistors, and wherein the solid-state multiphasic output circuit comprises an H-bridge, the plurality of resistors of the current limiting circuit including at least one resistor coupled in parallel with each of the legs of the H-bridge solid-state multiphasic output circuit.

11. The solid-state multiphasic defibrillator of claim 10, wherein the plurality of resistors of the current limiting circuit further include a resistor coupled across the first and second circuit nodes of the solid-state multiphasic output circuit.

12. The solid-state multiphasic defibrillator of claim 10, wherein the current limiting circuit further comprises a non-linear element coupled in series with one of the electrodes, the non-linear element restricting current flow below a threshold voltage, but allowing normal current flow above the threshold voltage.

13. The solid-state multiphasic defibrillator of claim 10, wherein the solid-state multiphasic output circuit includes a semiconductor switch, and the current limiting circuit includes a diode coupled in series with the semiconductor switch for preventing voltage breakdown across the output circuit when an external energy shock is applied to the output circuit from an outside source, such as from a second defibrillator.

14. A method for reducing leakage currents in a defibrillator, the defibrillator including an output circuit with first and second output nodes for conducting a defibrillation pulse to a patient, the method comprising:

(a) conducting a first current from the first output node in a first circuit path when the defibrillator is not applying a defibrillation pulse to a patient; and (b) conducting a second current from the second output node in a second circuit path when the defibrillator is not applying a defibrillation pulse to a patient wherein the first and second circuit paths are balanced by at least two resistors in series in each circuit path so as to reduce the voltage potential between the first and second output nodes and thereby reduce leakage currents that flow to the patient when the defibrillator is not applying a defibrillation pulse.

15. The method of claim 14, wherein the output circuit of the defibrillator comprises an H-bridge, and the first and second circuit paths comprise at least one resistive component coupled in parallel with each of the legs of the H-bridge.

* * * * *